United States Patent
Willbold et al.

(10) Patent No.: US 9,464,118 B2
(45) Date of Patent: *Oct. 11, 2016

(54) POLYMERS CONTAINING MULTIVALENT AMYLOID-BETA-BINDING D-PEPTIDES AND THEIR USE

(71) Applicant: FORSCHUNGSZENTRUM JUELICH GMBH, Juelich (DE)

(72) Inventors: Dieter Willbold, Juelich (DE); Susanne Aileen Funke, Sonnefeld (DE); Oleksander Brener, Duesseldorf (DE); Luitgard Nagel-Steger, Langenfeld (DE); Dirk Bartnik, Cologne (DE)

(73) Assignee: FORSCHUNGSZENTRUM JUELICH GMBH, Juelich (DE)

(*) Notice: Subject to any disclaimer, the term of this patent is extended or adjusted under 35 U.S.C. 154(b) by 0 days.

This patent is subject to a terminal disclaimer.

(21) Appl. No.: 14/388,869

(22) PCT Filed: Apr. 5, 2013

(86) PCT No.: PCT/EP2013/057161
§ 371 (c)(1),
(2) Date: Sep. 29, 2014

(87) PCT Pub. No.: WO2013/150127
PCT Pub. Date: Oct. 10, 2013

(65) Prior Publication Data
US 2015/0119336 A1    Apr. 30, 2015

(30) Foreign Application Priority Data

Apr. 5, 2012 (DE) .......... 10 2012 102 998
Sep. 14, 2012 (DE) .......... 10 2012 108 598
Sep. 14, 2012 (DE) .......... 10 2012 108 599

(51) Int. Cl.
*A61K 38/05* (2006.01)
*A61K 38/07* (2006.01)
(Continued)

(52) U.S. Cl.
CPC ............ *C07K 14/001* (2013.01); *C07K 7/06* (2013.01); *C07K 7/08* (2013.01); *C07K 14/4711* (2013.01); *G01N 33/6896* (2013.01); *G01N 2333/4709* (2013.01); *G01N 2800/2821* (2013.01)

(58) Field of Classification Search
None
See application file for complete search history.

(56) References Cited

U.S. PATENT DOCUMENTS 5,854,204 A   12/1998  Findeis et al.
5,968,820 A   10/1999  Zborowski et al.
(Continued)

FOREIGN PATENT DOCUMENTS

DE   10117281 A1   10/2002
DE   69621607 A1   1/2003
(Continued)

OTHER PUBLICATIONS

Willbold et al., EP1379546 B1 (English translation form WO2002081505A2).*
(Continued)

*Primary Examiner* — Jeffrey Stucker
*Assistant Examiner* — Aurora M Fontainhas
(74) *Attorney, Agent, or Firm* — Abel Law Group, LLP

(57) ABSTRACT

The invention relates to novel multivalent polymeric amyloid-beta-binding substances composed of several interconnected substances which per se already have amyloid-beta-binding properties, and to the use of these substances, referred to hereinbelow as "polymers", in particular in medicine.

18 Claims, 6 Drawing Sheets

(51) Int. Cl.
  *C07K 7/02* (2006.01)
  *C07K 14/00* (2006.01)
  *C07K 7/08* (2006.01)
  *C07K 14/47* (2006.01)
  *G01N 33/68* (2006.01)
  *C07K 7/06* (2006.01)

(56) References Cited

U.S. PATENT DOCUMENTS

| | | |
|---|---|---|
| 6,306,821 B1 | 10/2001 | Mikos et al. |
| 6,319,498 B1 | 11/2001 | Findeis et al. |
| 6,384,105 B1 | 5/2002 | He et al. |
| 6,423,790 B1 | 7/2002 | He et al. |
| 6,759,485 B2 | 7/2004 | He et al. |
| 7,658,917 B2 | 2/2010 | Findeis et al. |
| 7,951,796 B2 | 5/2011 | Korth et al. |
| 8,318,175 B2 | 11/2012 | Frangione et al. |
| 8,445,438 B2 | 5/2013 | Sundaram et al. |
| 2002/0022676 A1 | 2/2002 | He et al. |
| 2002/0098173 A1 | 7/2002 | Findeis et al. |
| 2002/0133001 A1 | 9/2002 | Gefter et al. |
| 2002/0177668 A1 | 11/2002 | He et al. |
| 2004/0005307 A1 | 1/2004 | Findeis et al. |
| 2005/0158306 A1 | 7/2005 | Halikas |
| 2007/0010435 A1 | 1/2007 | Frangione et al. |
| 2007/0092508 A1 | 4/2007 | Stein et al. |
| 2008/0051690 A1 | 2/2008 | Mattner et al. |
| 2009/0042211 A1 | 2/2009 | Birkmann et al. |
| 2009/0124001 A1 | 5/2009 | Korth et al. |
| 2009/0175853 A1 | 7/2009 | Frangione et al. |
| 2010/0166695 A1 | 7/2010 | Bundle et al. |
| 2011/0009343 A1 | 1/2011 | Findeies et al. |
| 2011/0189290 A1 | 8/2011 | Sundaram et al. |
| 2011/0201987 A1 | 8/2011 | Mattner et al. |
| 2011/0243949 A1 | 10/2011 | Willbold et al. |
| 2012/0226258 A1 | 9/2012 | Otto et al. |
| 2013/0045216 A1 | 2/2013 | Frangione et al. |
| 2013/0143822 A1 | 6/2013 | Funke et al. |

FOREIGN PATENT DOCUMENTS

| | | |
|---|---|---|
| DE | 102005009909 A1 | 9/2006 |
| DE | 60026983 T2 | 1/2007 |
| DE | 102005031429 A1 | 1/2007 |
| DE | 102005063175 A1 | 2/2007 |
| DE | 102006015140 A1 | 10/2007 |
| DE | 102008037564 A1 | 5/2010 |
| DE | 102009037015 A1 | 2/2011 |
| DE | 102010019336 A1 | 11/2011 |
| DE | 102010017130 A1 | 12/2011 |
| EP | 1379546 * | 6/2007 |
| WO | 0242462 A2 | 5/2002 |
| WO | 02081505 A2 | 10/2002 |
| WO | 2004056318 A2 | 7/2004 |
| WO | 2006005706 A2 | 1/2006 |
| WO | 2007047967 A2 | 4/2007 |
| WO | 2008116293 A2 | 10/2008 |
| WO | 2010062570 A2 | 6/2010 |
| WO | 2011147797 A2 | 12/2011 |
| WO | 2013150126 A2 | 10/2013 |
| WO | 2013150127 A2 | 10/2013 |

OTHER PUBLICATIONS

Zhang Guobao et al: "Multiple-peptide conjugates for binding beta-amyloid plaques of Alzheimer's disease", Bioconjugate Chemistry, ACS, Washington, DC, US, vol. 14, No. 1, Jan. 1, 2003, pp. 86-92.

Katja Wiesehan et al: "Selection of D-Amino-Acid Peptides That Bind to Alzheimer's Disease Amyloid Peptide A [beta]42 by Mirror Image Phage Display", Chembiochem, vol. 4, No. 8, Aug. 4, 2003, pp. 748-753.

Sidhartha M. Chafekar et al: "Branched KLVFF Tetramers Strongly Potentiate Inhibition of [beta]-Amyloid Aggregation", Chembiochem, vol. 8, No. 15, Oct. 15, 2007, pp. 1857-1864.

Stains Cliff I et al: "Molecules that target beta-amyloid", Chemmedchem, Wiley-VCH Verlag., Weinheim, DE, vol. 2, No. 12, Dec. 1, 2007, pp. 1675-1692.

Funke Susanne Aileen et al: "Peptides for Therapy and Diagnosis of Alzheimer's Disease", Current Pharmaceutical Design, Bentham Science Publishers, NL, vol. 18, No. 6, Feb. 1, 2012, pp. 755-767.

Ranjini K. Sundaram et al: "Novel Detox Gel Depot Sequesters [beta]-Amyloid Peptides in a Mouse Model of Alzheimer's Disease", International Journal of Peptide Research and Therapeutics, vol. 18, No. 2, Nov. 23, 2011, pp. 99-106.

Andreas Müller-Schiffmann et al: "Combining Independent Drug Classes into Superior, Synergistically Acting Hybrid Molecules", Angewandte Chemie International Edition, vol. 49, No. 46, Nov. 8, 2010, pp. 8743-8746.

Dirk Bartnik et al: "Differently selected D-enantiomeric peptides act on different A.beta. species", Rejuvenation Research, Mary Ann Liebert, New Rochelle, NY, US, vol. 13, No. 2-3, May 12, 2010, pp. 202-205.

Susanne Aileen Funke et al: "Mirror image phage display-a method to generate d-peptide ligands for use in diagnostic or therapeutical applications", Molecular Biosystems, vol. 5, No. 8, Jan. 1, 2009, p. 783.

* cited by examiner

POLYMERS CONTAINING MULTIVALENT AMYLOID-BETA-BINDING D-PEPTIDES AND THEIR USE

SEQUENCE LISTING

The instant application contains a Sequence Listing which has been submitted electronically in ASCII format and is hereby incorporated by reference in its entirety. Said ASCII copy, created on Jan. 6, 2015, is named Sequ List ASCII Jun. 1, 2015FZJ1201PCTUS and is 12,699 bytes in size.

BACKGROUND OF THE INVENTION

1. Field of the Invention

The present invention relates to novel multivalent polymeric amyloid-beta-binding substances composed of several interconnected substances which per se already have amyloid-beta-binding properties, and to the use of these substances, referred to hereinbelow as "polymers", in particular in medicine.

2. Discussion of Background Information

Owing to the demographic development in the coming decades, the number of persons who suffer from age-related diseases will increase. Alzheimer's disease (AD, Alzheimer's dementia, Latin=morbus Alzheimer) must be mentioned in particular in this context.

No active substance or medicament exists to date that acts against the causes of AD. The medicaments which have been approved and employed to date alleviate some of the symptoms which occur in Alzheimer's dementia, but are not capable of slowing down the progression of the disease or of bringing about a recovery. Some substances exist which have been successful in animal experiments in the prevention, but not (necessarily) in the treatment of AD. Active substances against neurodegenerative diseases are known from DE 10 2006 015 140 A1.

One feature of Alzheimer's disease are extracellular deposits of amyloid-beta peptide (A-beta peptide, Aβ or Aβ peptide). These deposits of the A-beta peptide in plaques can typically be found post mortem in the brains of AD patients. This is why various forms of the A-beta peptide—such as, for example, fibrils—are held responsible for the development and progression of the diseases. In addition, the small, freely-diffusible A-beta oligomers have been considered for some years to be the main cause for the development and progress of AD.

A-beta monomers, being units of the A-beta oligomers, are constantly being generated in the human body and, probably, are not toxic per se. Indeed, it is possible that monomers exert a positive function. Depending on their concentration, A-beta monomers can undergo random association. The concentration depends on their rate of generation and degradation in the body. If, with increasing age, the concentration of A-beta monomers in the body increases, spontaneous association of the monomers to give rise to A-beta oligomers becomes more and more probable. The resulting A-beta oligomers might multiply analogously to prions and, ultimately, result in Alzheimer's disease.

An important difference between the prevention and treatment or indeed cure of AD is the fact that prevention might possibly already be achieved by preventing the first A-beta oligomers from being formed. To this end, some few A-beta ligands with low affinity and with selectivity for the A-beta oligomers will suffice.

The formation of A-beta oligomers from a large number of monomers is a high-order reaction and, therefore, dependent to a higher power of the A-beta monomer concentration. Thus, even a small reduction in the active A-beta monomer concentration will lead to the formation of the first A-beta oligomers being prevented. It is probable that the—rather preventative—therapeutic concepts and substances which are currently being developed are based on this mechanism.

In the treatment of AD, however, one will have to depart from a completely different situation. In this case, A-beta oligomers or, possibly, even larger polymers or fibrils exist, which multiply by prion-like mechanisms. This multiplication, however, is a low-order reaction and dependent from the A-beta monomer concentration to a minor degree only.

The prior-art substances reduce the A-beta monomer and/or oligomer concentration in very different ways. Thus, for example, gamma-secretase modulators are known which have been employed for preventative purposes in animal experiments.

WO 02/081505 A2 discloses various sequences of D-amino acids which bind to A-beta peptides. These D-amino acid sequences bind to amyloid-beta peptides with a dissociation constant ($K_D$ value) of 4 µM.

WO 2011/147797 A2 discloses hybrid compounds composed of aminopyrazols and peptides, which hybrid compounds prevent the oligomerization of A-beta.

Compounds which interact with A-beta peptides are disclosed from DE 10 2008 037 564 A1, DE 696 21 607 T2 or DE 10 2010 019 336 A1. The binding of a multivalent polymer to two binding partners is described in WO 2008/116293 A1.

In the case of many substances which have demonstrated positive results in animal experiments it has not been possible to confirm this activity in clinical studies on humans. Clinical phase-II and III studies only allow the treatment of humans where AD has been diagnosed unambiguously. In this case, a small reduction of the A-beta monomer concentration will no longer suffice for preventing that the already existing A-beta oligomers give rise to even more of the same, for example by a prion-like mechanism. The multiplication of the A-beta oligomers or, even better, their destruction or neutralization is, however, essential to influence the pathogenesis.

To date, Alzheimer's dementia is mainly diagnosed by neuropsychological tests, by experiments on persons where symptoms of dementia have been identified. However, it is known that A-beta oligomers and the subsequently following fibrils and plaques originate up to 20 years before symptoms are observed in the patient's brain, and may already have caused irreversible damage. However, it has not been possible to date to diagnose AD before the onset of symptoms.

Therefore, there remains a need for novel compounds (active substances) which bind to A-beta oligomers in a highly specific manner and with high affinity, therefore preventing their multiplication. It is intended that these compounds do not cause any effects with undesired side-effects, in particular no immune reaction. It is furthermore intended that the compounds recognize, completely destroy and/or prevent the (prion-like) multiplication of, toxic A-beta oligomers and therefore even the small, freely-diffusible oligomers even at low concentrations.

Furthermore, there is also a need for novel compounds which can be employed as probes for recognizing and labeling A-beta oligomers, in particular when these oligomers are only present at low concentrations.

SUMMARY OF THE INVENTION

This object is achieved by the polymers according to the invention, which comprise at least two substances (monomers) which bind to amyloid-beta oligomers.

For the purposes of the present invention, the term A-beta oligomers refers both to A-beta aggregates and to A-beta oligomers and also to small, freely-diffusing A-beta oligomers. Polymers, for the purposes of the invention, is a substance formed by 2, 3, 4, 5, 6, 7, 8, 9, 10, 11, 12, 13, 14, 15, 16, 17, 18, 19 or 20 substances (monomers) which per se already bind amyloid-beta, or multiples of these substances.

In a first embodiment, the polymers are peptides. They are preferably essentially composed of D-amino acids.

For the purposes of the present invention, the expression "essentially of D-amino acids" means that the monomers to be employed are composed to at least 60%, preferably 75%, 80%, especially preferably 85%, 90%, 95%, in particular 96%, 97%, 98%, 99%, 100% of D-amino acids.

In a variant of the invention, monomers are used which binds to an A-beta monomer and/or A-beta oligomers and/or fibrils of the A-beta peptide with a dissociation constant ($K_D$ value) of not more than 500 µM, preferably 250, 100, 50 µM, especially preferably 25, 10, 6 µM, in particular 4, 2, 1 µM.

The polymer according to the invention comprises 2, 3, 4, 5, 6, 7, 8, 9, 10 or more of the above-described monomers.

In a further embodiment, the monomers are selected from the group consisting of: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64. SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78 and SEQ ID NO:79 and homologs thereof.

In a further variant, the polymers according to the invention bind to parts of the amyloid beta peptide.

In a further variant, the monomers have sequences which differ by up to three amino acids from the abovementioned sequences.

Furthermore, sequences which comprise the abovementioned sequences are also employed as monomers.

In a further variant, the monomers include fragments of the abovementioned sequences or include sequences which are homologous to the abovementioned sequences.

According to the invention, "homologous sequences" or "homologs" means that an amino acid sequence has an identity to one of the abovementioned amino acid sequence of the monomers of at least 50, 55, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100%. Instead of the term "identity", the terms "homologous" or "homology" are used synonymously in the present description. The identity between two nucleic acid sequences or polypeptide sequences is calculated by comparison with the aid of the BESTFIT program based on the algorithm of Smith, T. F. and Waterman, M. S (Adv. Appl. Math. 2: 482-489 (1981)), setting the following parameters for amino acids: gap creation penalty: 8 and gap extension penalty: 2; and the following parameters for nucleic acids: gap creation penalty: 50 and gap extension penalty: 3. The identity between two nucleic acid sequences or polypeptide sequences is preferably defined by the identity of the nucleic acid sequence/polypeptide sequence over the in each case entire sequence length, as calculated by comparison with the aid of the GAP program based on the algorithm of Needleman, S. B. and Wunsch, C. D. (J. Mol. Biol. 48: 443-453) setting the following parameters for amino acids: gap creation penalty: 8 and gap extension penalty: 2; and the following parameters for nucleic acids: gap creation penalty: 50 and gap extension penalty: 3.

For the purposes of the present invention, two amino acid sequences are identical when they have the same amino acid sequence.

Homologs are to be understood in a variant as the corresponding retro-inverse sequences of the abovementioned monomers. According to the invention, the term "retro-inverse sequence" refers to an amino acid sequence which is composed of amino acids in the enantiomeric form (inverse: the chirality of the alpha-C atom is inverted) and in which the sequence order to the original amino acid sequence has additionally been reversed (retro=backwards).

The polymer according to the invention is composed of identical monomers, or comprises different monomers.

In one alternative, the polymer according to the invention is composed of any desired combination of 2, 3, 4, 5, 6, 7, 8, 9, 10 or more of the above-described monomers.

In one embodiment, the polymer according to the invention is a dimer of two D3 monomers (SEQ ID NO:13).

In a further embodiment, the polymer according to the invention is a dimer of two RD2 monomers (SEQ ID NO:76).

Dimers can be prepared for example via chemical synthesis or peptide synthesis.

In one embodiment of the invention, the monomers are covalently linked to each other. In a further embodiment, the monomers are noncovalently linked to each other.

For the purposes of the invention, a covalent linkage or bond, of the monomer units exists when the peptides are linked with each other head-to-head, tail-to-tail or head-to-head in a linear fashion without interposed linker or linker groups being employed.

For the purposes of the invention, a noncovalent linkage exists when the monomers are linked to each other via biotin and streptavidin, in particular streptavidin tetramer.

In one variant of the present invention, the monomers may be linked to each other in a linear fashion, in particular as described hereinabove. In another variant, the monomers are linked with each other in a branched fashion to give the polymer according to the invention.

According to the invention, a branched polymer may be a dendrimer in which the monomers are covalently or noncovalently linked to each other.

Alternatively, the monomers may also be linked to a platform molecule (such as, for example, PEG or sugar), thus forming a branched polymer.

As an alternative, combinations of these options are also possible.

The polymer according to the invention is characterized in that it binds amyloid-beta oligomers with a dissociation constant of not more than 1 µM, preferably 800, 600, 400, 200, 100, 10 nM, especially preferably, 1000, 900, 800, 700, 600, 500, 400, 300, 200, 100, 50 pM, in particular not more than 20 pM. In a further embodiment, the polymer according to the invention is characterized in that it binds amyloid-beta oligomers with a dissociation constant of not more than 1 mM, preferably 800, 600, 400, 200, 100, 10 µM, especially preferably 1000, 900, 800, 700, 600, 500, 400, 300, 200, 100, 50 nM, particularly preferably 1000, 900, 800, 700, 600, 500, 400, 300, 200, 100, 50 pM, most preferably not more than 20 pM, in particular 15, 10, 9, 8, 7, 6, 5 pM.

The polymer according to the invention is suitable for use in medicine.

In one embodiment, the polymer is a polymer for the treatment of Alzheimer's disease. In a further embodiment, it is a polymer which can be employed for the treatment of Parkinson's disease, CJD (Creutzfeldt Jakob Disease) or diabetes.

The polymers, composed in accordance with the invention of monomers which, in turn, bind to A-beta oligomers, show pronounced synergistic effects in respect of their selectivity and affinity to the A-beta oligomers in comparison with the monomers. In other words: the polymers according to the invention outperform the monomers. For the purposes of the present invention, synergistic effects are effects which demonstrate higher selectivity and affinity in respect of the A-beta oligomers, in particular of the $K_D$ value regarding the binding to A-beta oligomers, than the monomers individually or in their addition.

A linker is to be understood to be one or more molecules which are bonded to the monomers via covalent bonds, it also being possible for these linkers to be linked to each other by covalent bonds.

In one alternative of the present invention, the properties of the polymer, that is to say the binding to A-beta oligomers, which are predefined by the monomers are not modified by the linkers.

In a further alternative, the linkers bring about a modification of the properties of the polymer, which properties are predefined by the monomers. In such an embodiment, the selectivity and/or affinity of the polymers according to the invention in respect of the A-beta oligomers is pronounced and/or the dissociation constant is reduced. In a further embodiment, the linkers are chosen such that, or may be arranged such that, they modify the steric effect of the polymers according to the invention in such a way that the latter bind selectively only to A-beta oligomers of a specific size.

A nonlimiting example of a linker is the amino acid sequence "nwn".

Such a modification of the steric effect of the polymers according to the invention may also be achieved by the composition of branched polymers according to the invention, by dendrimers with a specific composition or the corresponding composition of the polymer by means of monomers and a platform molecule, or combinations of these options.

Another subject matter of the present invention is a composition comprising the polymer according to the invention, in particular for the treatment of Alzheimer's disease.

A further subject matter of the present invention is a composition comprising the polymer according to the invention, in particular for the prevention of toxic A-beta oligomers or for the destruction of polymers or fibrils formed thereby.

The "composition" according to the invention may be for example a vaccine, a medicament (for example in the form of tablets), a solution for injection, a foodstuff or food supplement, comprising the polymer according to the invention in a formulation to be prepared based on expert knowledge.

The polymers according to the invention detoxify the A-beta oligomers or polymers formed thereof, and also fibrils, by binding to them and therefore converting them into nontoxic compounds. Substances which are capable of inhibiting the formation of fibrils need not necessarily also be capable of destroying previously formed fibrils since previously formed A-beta fibrils are highly stable and can only be destroyed with great difficulty and very slowly. Accordingly, another subject matter of the present invention is a method of detoxifying the A-beta oligomers, polymers or fibrils formed therefrom.

Owing to their property of binding not only the small, freely diffusible A-beta oligomers, larger A-beta oligomers up to fibrils, the polymers according to the invention can be employed at all stages of AD. Based on the teaching of the present invention, it is possible to prepare polymers which also selectively bind to various forms of the A-beta oligomers.

Another, further subject matter of the present invention is a process for the preparation of the polymer according to the invention. Preferred processes are, for example, peptide synthesis methods (peptides), the recombinant preparation of proteins, and accepted organic synthesis methods for any compounds known as low-molecular-weight compounds.

The present invention also relates to the use of the polymer as probe for the identification, qualitative and/or quantitative determination of amyloid-beta oligomers. Another subject matter of the present invention is a probe, comprising the polymer according to the invention, for identification, qualitative and/or quantitative determination of amyloid-beta oligomers.

Such probes are of great importance since they allow an early diagnosis of Alzheimer's dementia. This means that the disease can be tackled even at a very early stage.

Such molecular probes comprise the polymer according to the invention and may be injected to the patients, for example via the intravenous route. Further components of the probes may be: colorants, fluorescent dyes, radioactive isotopes (for example PET), gadolinium (MRI) and/or components which are employed for probes in imaging. After crossing the blood-brain-barrier, the probes may bind to A-beta oligomers and/or plaques. The A-beta oligomers and/or plaques labeled thus can be visualized by means of imaging techniques such as, for example, SPECT, PET, CT, MRT, proton MR spectroscopy and the like.

A further subject matter of the present invention is the use of the polymer for preventing the multiplication of toxic amyloid-beta oligomers.

Furthermore, the polymers according to the invention are also employed for imaging nontoxic polymer-amyloid-beta oligomer complexes.

A further subject matter of the present invention is a kit comprising the polymer according to the invention. In such a kit, the polymers according to the invention may be packaged in containers, optionally with/in buffers or in solutions. All components of the kit can be packaged in the same container or separate from each other. Furthermore, the kit may comprise instructions for its use. Such a kit may, for example, comprise the according to the invention in a vial equipped with stopper and/or septum. Furthermore, it may also comprise a disposable syringe, for example.

Sequences which can be employed in accordance with the invention are shown hereinbelow:

```
RD 2:
                              (SEQ ID NO: 1)
ptlhthnrrrrr

D3D3:
                              (SEQ ID NO: 13)
rprtrlhthnrrprtrlhthrnr

D3nwnD3:
                              (SEQ ID NO: 14)
rprtrlhthrnrnwnrprtrlhthrnr double-D3-free-Ntermini:
                              (SEQ ID NO: 15)
(rprtrlhthrnr)₂-PEG3 double-D3-free-Ctermini:
                              (SEQ ID NO: 16)
PEG5-(rprtrlhthrnr)₂

(SEQ ID NO: 2)
kqhhveygsdhrfead (SEQ ID NO: 3)
shyrhisp (SEQ ID NO: 4)
giswqqshhlva (SEQ ID NO: 5)
prtrlhth (SEQ ID NO: 6)
qshyrhispaqv (SEQ ID NO: 7)
qshyrhispdqv (SEQ ID NO: 8)
qshyrhispar (SEQ ID NO: 9)
kshyrhispakv (SEQ ID NO: 10)
rprtrlhthrnr (SEQ ID NO: 11)
rprtrlhthrte (SEQ ID NO: 12)
kprtrlhthrnr (SEQ ID NO: 17)
daefrhdsgye (SEQ ID NO: 18)
hhghspnvsqvr (SEQ ID NO: 19)
gsfstqvgslhr (SEQ ID NO: 20)
htgtqsyvprl (SEQ ID NO: 21)
tlayaraymvap (SEQ ID NO: 22)
tlayaraymvap (SEQ ID NO: 23)
atpqndlktfph (SEQ ID NO: 24)
tqpetdllrvqf
```

-continued

```
                              (SEQ ID NO: 25)
citwpptglty (SEQ ID NO: 26)
tfletgpiyadg (SEQ ID NO: 27)
Ivppthrhwpvt (SEQ ID NO: 28)
appgnwrnylmp (SEQ ID NO: 29)
dnysnyvpgtkp (SEQ ID NO: 30)
svsvgmkpsprp (SEQ ID NO: 31)
slpnpfsvssfg (SEQ ID NO: 32)
yvhnpyhlpnpp (SEQ ID NO: 33)
crrlhtyigpvt (SEQ ID NO: 34)
gatmkkmddhtv (SEQ ID NO: 35)
Igktqklsdahs (SEQ ID NO: 36)
ddqarpymaygp (SEQ ID NO: 37)
gdtwvnmvsmvh (SEQ ID NO: 38)
gytwvnmvsmvh (SEQ ID NO: 39)
wtntvarlatpy (SEQ ID NO: 40)
qtqalyhsrqvh (SEQ ID NO: 41)
nsqtqtlhlfph (SEQ ID NO: 42)
hntsanilhssh (SEQ ID NO: 43)
shinptsfwpap (SEQ ID NO: 44)
tfsnplymwprp (SEQ ID NO: 45)
gpspfnpqptpv (SEQ ID NO: 46)
fsdhksptpppr (SEQ ID NO: 47)
stsvypppsaw (SEQ ID NO: 48)
yglptqansmql (SEQ ID NO: 49)
hnrtdntyirpt (SEQ ID NO: 50)
lqqplgnnrpns (SEQ ID NO: 51)
kpedsaaypqnr
``` rpedsvitktqnt (SEQ ID NO: 52)

raadsgctptkh (SEQ ID NO: 53)

rprtrlhthrnt (SEQ ID NO: 54)

rprtrlhthtnv (SEQ ID NO: 55)

rprtrlhthtnr (SEQ ID NO: 56)

rprtrlhthrkq (SEQ ID NO: 57)

rprtrlhtlrnr (SEQ ID NO: 58)

rrrsplhthrnr (SEQ ID NO: 59)

lrsprqrripri (SEQ ID NO: 60)

rkrqlrmttprp (SEQ ID NO: 61)

shyrhispaqk (SEQ ID NO: 62)

double-D3-free-Ntermini:
(rprtrlhthrnr)2- (SEQ ID NO: 63)

double-D3-free-Ctermini:
(rprtrlhthrnr)2 (SEQ ID NO: 64)

DB 3:
rpitrlrthqnr, (SEQ ID NO: 65)

D3:
rprtrlhthrnr (SEQ ID NO: 66)

RD 1:
pnhhrrrrrrtl (SEQ ID NO: 67)

RD 3:
rrptlrhthnrr (SEQ ID NO: 68)

D3-delta-hth:
rprtrlrnr (SEQ ID NO: 69)

NT-D3:
rprtrl (SEQ ID NO: 70)

DB 1:
rpitrlhtnrnr, (SEQ ID NO: 71)

DB 2:
rpittlqthqnr, (SEQ ID NO: 72)

DB 4:
rprtrlrthqnr (SEQ ID NO: 73 ())

DB 5:
rpitrlqtheqr (SEQ ID NO. 74)

D3-delta-hth D3-delta-hth:
rprtrlrnrrprtrlrnr (SEQ ID NO: 75)

RD 2-RD 2:
ptlhthnrrrrrptlhthnrrrrr (SEQ ID NO: 76)

DO 3:
sgwhynwqywwk (SEQ ID NO: 77)

rprtrsgwhynwqywwkrnr (SEQ ID NO: 78)

ptlsgwhynwqywwkrrrrr (SEQ ID NO: 79)

Antibodies which bind to A-beta are shown hereinbelow:
Antibodies which
a) bind to a retro-inverse sequence of the amyloid-beta peptide or amyloid-beta peptide subfragments and/or
b) which bind to the multimerization domain of the amyloid-beta peptide and also to the amyloid-beta peptide and/or
c) which bind to one of the abovementioned sequences according to the invention, selected from the following group:
SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64. SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78 and SEQ ID NO:79 or to homologous sequences thereof.

BRIEF DESCRIPTION OF THE DRAWINGS

In the accompanying drawings,
FIG. 1 graphically represents the relative fluorescence obtained with several substances in the thioflavin-T assay described in Example 2 below.

DETAILED DESCRIPTION OF THE PRESENT INVENTION

EXAMPLES

Example 1

The following four D3 dimers were prepared:

```
D3D3:
                              (SEQ ID NO: 13)
rprtrlhthrnrrprtrlhthrnr D3nwnD3:
                              (SEQ ID NO: 14)
rprtrlhthrnrnwnrprtrlhthrnr double-D3-free-Ntermini:
                              (SEQ ID NO: 15)
(rprtrlhthrnr)₂-PEG3 double-D3-free-Ctermini:
                              (SEQ ID NO: 16)
PEGS-(rprtrlhthrnr)₂
```

Furthermore, dimers were prepared (via chemical synthesis or peptide synthesis) which are composed of D3 and D1 (sequence qshyrhispaqv, SEQ ID NO:6) or D3 and V1, where V1 a variant of D1 with deletion of the first amino acid at the N terminus (sequence shyrhispaqk, SEQ ID NO:62)
D3D1
D3V1
V1 D3

Example 2

Thioflavin T assay

The D3 dimers prepared in Example 1 as well as a D3 monomer were compared in a conventional thioflavin-T-(ThT) assay which is known to a person skilled in the art. ThT is a dye which, when bound to regular fibrils, demonstrates higher fluorescence and is therefore used as a measure for fibrilation. The D3 dimers reduced A-beta fibrilation much more efficiently than the D3 monomer.

Figure 1:
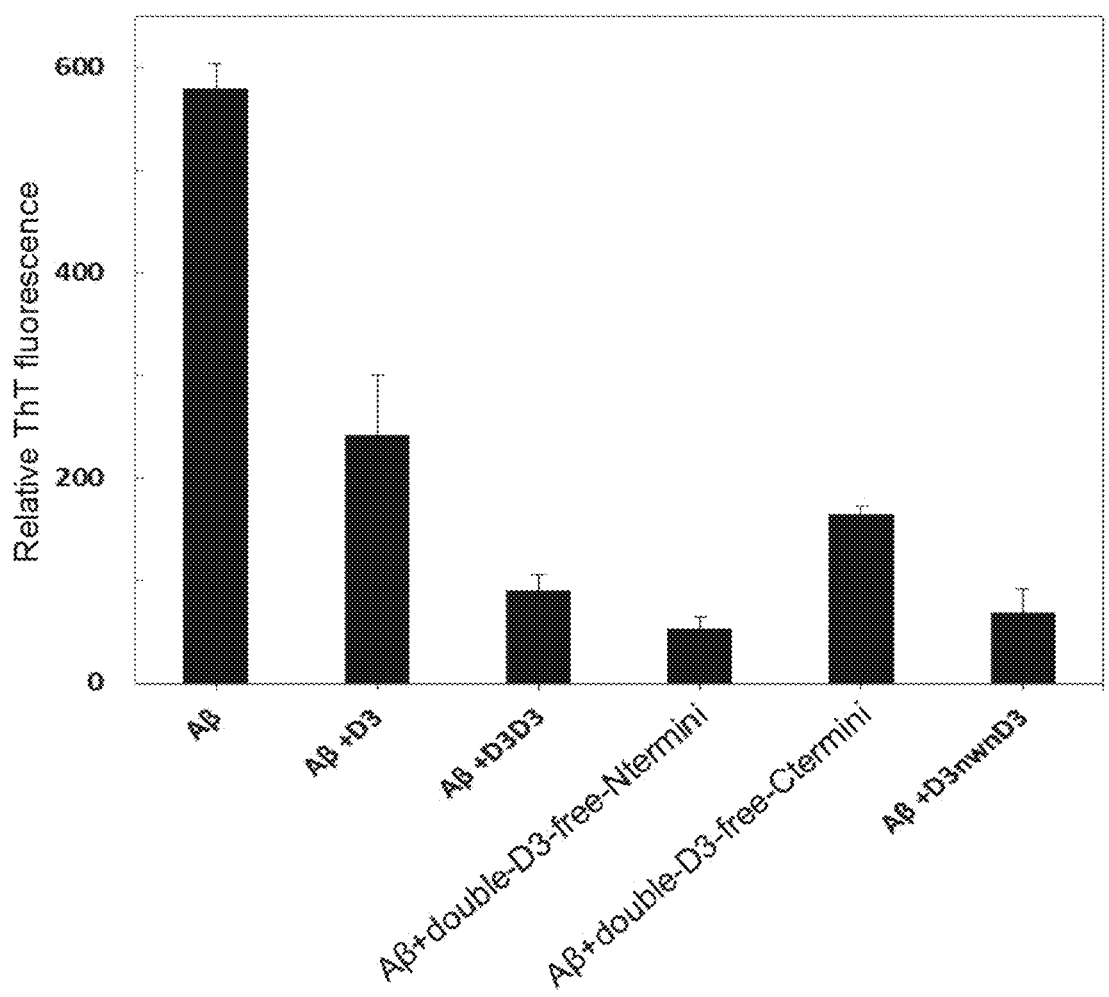

FIG. 1 shows the results of the ThT assay for analyzing the aggregation behavior of A-beta 1-42 in the presence of D3 and of D3 multimers. A-beta pellets were prepared by preincubation with HFIP overnight and subsequent evaporation by means of a vacuum centrifuge (222 μM Aβ in HFIP). A-beta pellets were resuspended in 250 μL PBS pH 7.4 (including 10 μM ThT and 10 μM D3 or D3 multimer) and divided into aliquots for a determination in quadruplicate. ThT fluorescence was measured in a fluorescence spectrometer at $\lambda$ex 440 nm and $\lambda$em =490 nm.

Example 3

The D3D1 dimers prepared in Example 1 as well as the D1 and D3 monomers were compared in a conventional ThT assay ChTThT assay which is known to a person skilled in the art.

The D3D1 dimers were reduced the A-beta fibrilation much more efficiently than the D3 monomer.

Figure 2:
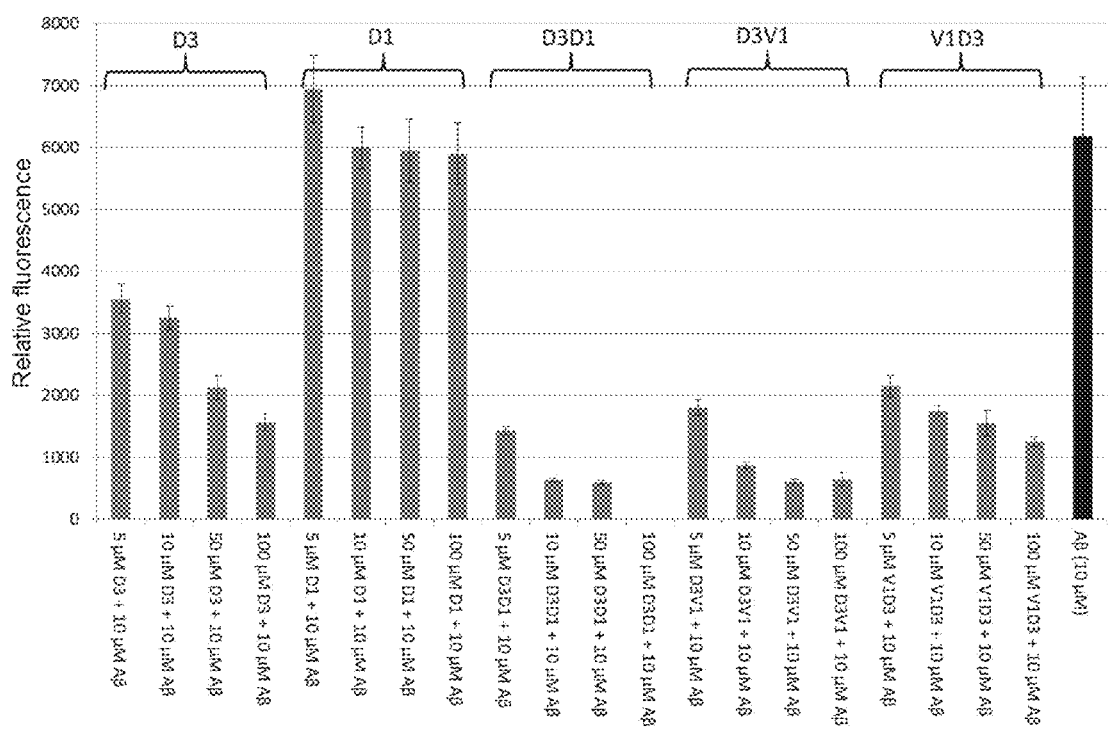
FIG. 2 graphically represents the relative fluorescence obtained with several substances in the thioflavin-T assay described in Example 3 below.

FIG. 2 shows the results of the ThT assay for analyzing the aggregation behavior of A-beta1-42 in the presence of D3 and D1 or of D3D1 multimers. A-beta was preincubated overnight in HFIP (222 μM A-beta in HFIP). Thereafter, aliquots of 13.5 μg were prepared, and the HFIP was evaporated overnight. A-beta pellets were resuspended in 270 μL PBS pH 7.4 (including 10 μM ThT), and the respective concentration of D3 or D3D1 multimer (5 μM, 10 μM, 50 μM or 100 μM) was subsequently added, and the mixtures were then divided into aliquots for a determination in quintuplicate. ThT fluorescence was measured in a fluorescence spectrometer at $\lambda$ex 440 nm and $\lambda$em=490 nm.

Example 4

Figure 3:
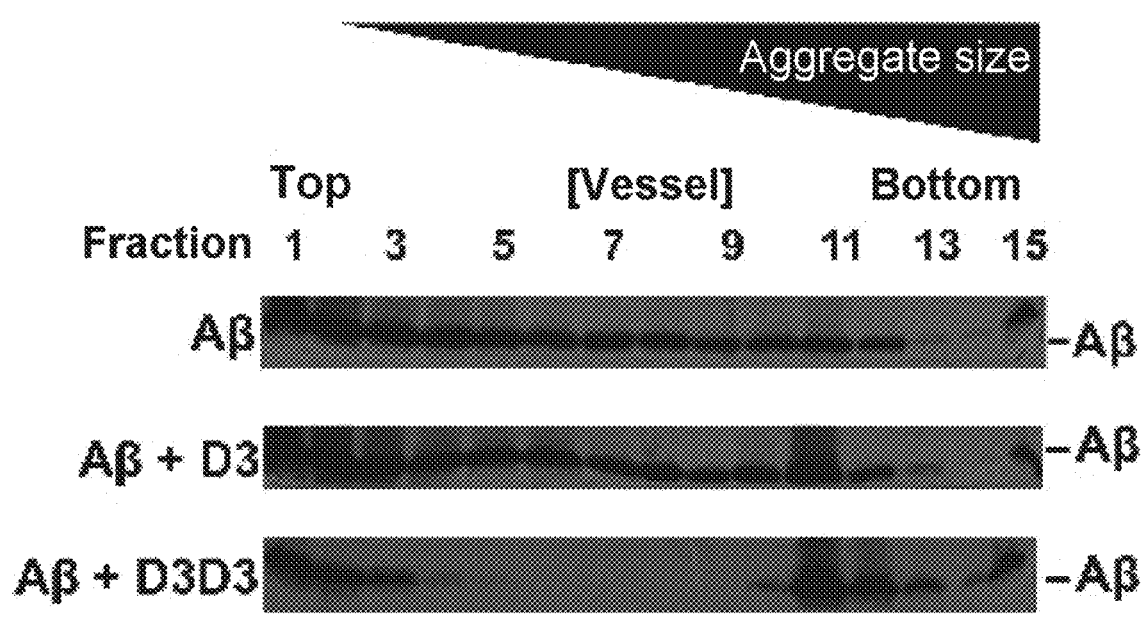
FIG. 3 graphically represents the results of a size distribution analysis of A-beta samples described in Example 4 below.

The D3 dimers prepared in Example 1 and the D3 monomer were mixed with Abeta1-42 and subjected to a density gradient centrifugation. In this procedure, the size distributions of A-beta in solution and of A-beta peptide mixtures were studied by sedimentation analysis in an Iodixanol gradient (5-50%). The mixtures comprised 80 μM A-beta and 20 (D3) or 10 (D3D3) μM peptide. After centrifugation, 15 fractions of in each case 140 μl were obtained by sequential pipetting from the surface and analyzed by means of denaturing polyacrylamide gel electrophoresis (SDS-PAGE) followed by silver staining. The results (FIG. 3) show that the peptides significantly reduce the A-beta oligomer content (fractions 4-10), D3D3 at the point in time of the investigation to a much higher degree than D3. Large aggregates which can be detected in fractions 12-15 are generated. Further investigations revealed that D3-A-beta oligomers precipitated and converted into large amorphous and nontoxic aggregates (Funke et al., ACS Chem. Neurosci. 2010).

Example 5

Substances according to the invention are capable of inhibiting the formation of fibrils and of destroying preformed fibrils. The efficiency of inhibitor dimers (D3D3 SEQ ID NO: 13, RD2RD2 SEQ ID NO: 76, D3(Δ)delta-hthD3(Δ)delta-hth SEQ ID NO: 75) in a thioflavin T (ThT) disfibrilation assay was studied in comparison with the corresponding inhibitor monomers (D3 SEQ ID NO: 66, RD2 SEQ ID NO: 1, D3(Δ)delta-hth SEQ ID NO: 69).

What is studied here is the extent of preformed ThT-positive fibrils which is reduced after a specific incubation period. Thioflavin T (ThT), upon interaction with amyloid ThT-positive fibrils, measurably changes its spectroscopic properties. The decrease in the measured ThT fluorescence ($\lambda$em: 450 nm, $\lambda$ex: 490 nm) reflects a decrease in β-sheet structures, which are characteristic of Abeta fibrils.

To prepare preformed A-beta fibrils, 33 μM of synthetic Abeta(1-42) were incubated for 6 days in 10 mM sodium phosphate pH 7.4 and 8.5% DMSO at 37° C. The resulting Abeta fibrils were combined with 0.1 μg/μl of the respective substance (D3D3, RD2RD2, D3delta-hthD3delta-hth, D3, RD2, DΔhth) and 10 μM ThT to give 20 μM. 50 μL of each batch were placed into a well of a black microtiter plate with 384 wells (Nunc, Langenselbold). The ThT fluorescence was monitored over 17.5 h. While doing so, the microtiter plate was shaken for 30 s before each measurement. All samples were measured in quintuplicate.

When evaluating the assay, the mean, the standard deviation and the significance (between monomeric and dimeric effectors) were determined. The ThT fluorescence of the effectors was standardized to the ThT fluorescence of Abeta fibrils in the absence of inhibitor substances.

Figure 4:
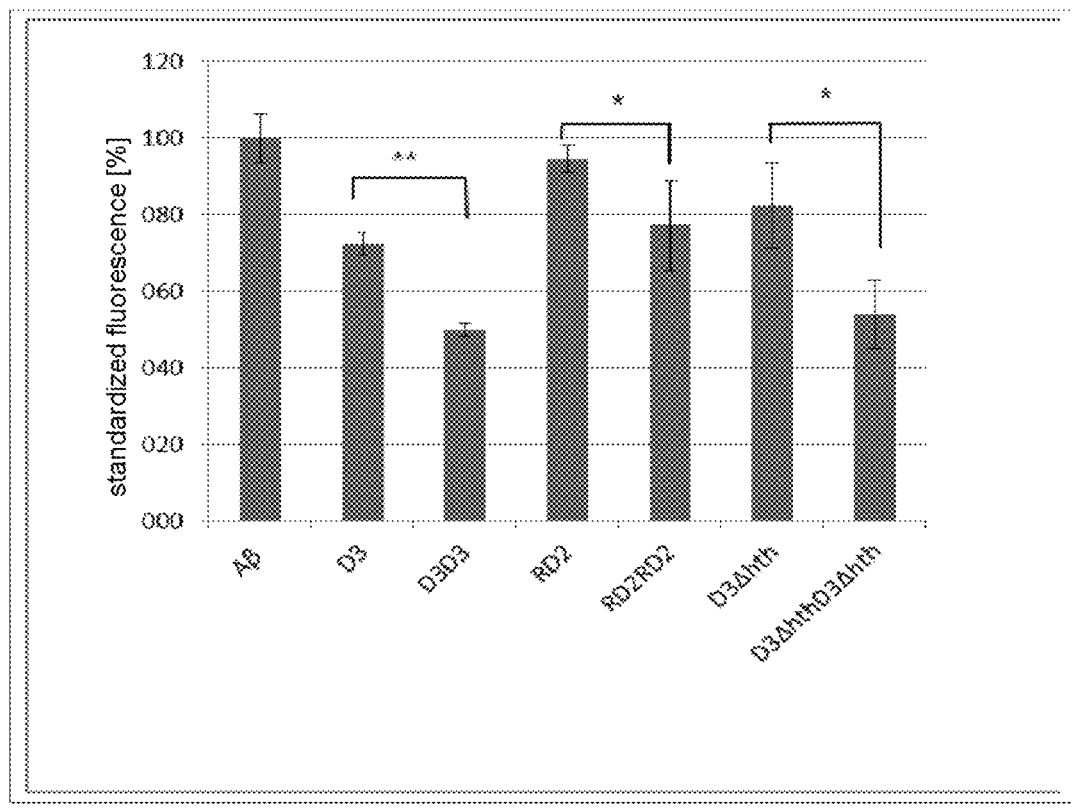
FIG. 4 graphically represents the standardized fluorescence obtained with several inhibitor substances in the thioflavin-T assay described in Example 5 below.

All the tested inhibitor substances showed a decrease in ThT fluorescence (FIG. 4). This demonstrates that all of them were capable of converting preformed A-beta fibrils into non-fibril-like A-beta species. In this context, the dimeric substances D3D3, RD2RD2 and D3delta-hthD3delta-hth demonstrated a significantly more pronounced effect in comparison with the monomeric peptides D3, RD2 and D3delta-Δhth. The significance was determined by the Mann-Whitney test and is shown in the figure by asterisks: *, p<0.05; **, p<0.01.

Example 6

Figure 5:
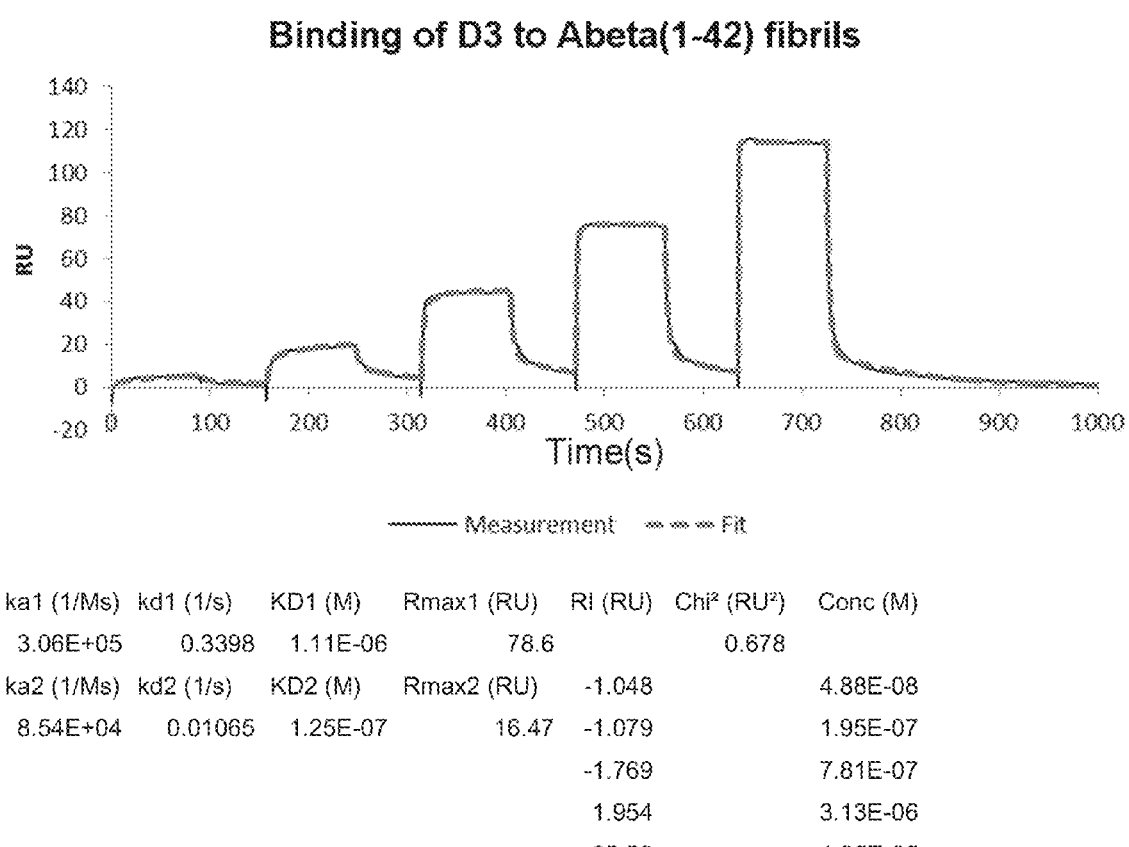
FIGS. 5 and 6 are graphs showing sensorgrams and fit curves obtained from the experiments described in Example 6 below.
Figure 6:
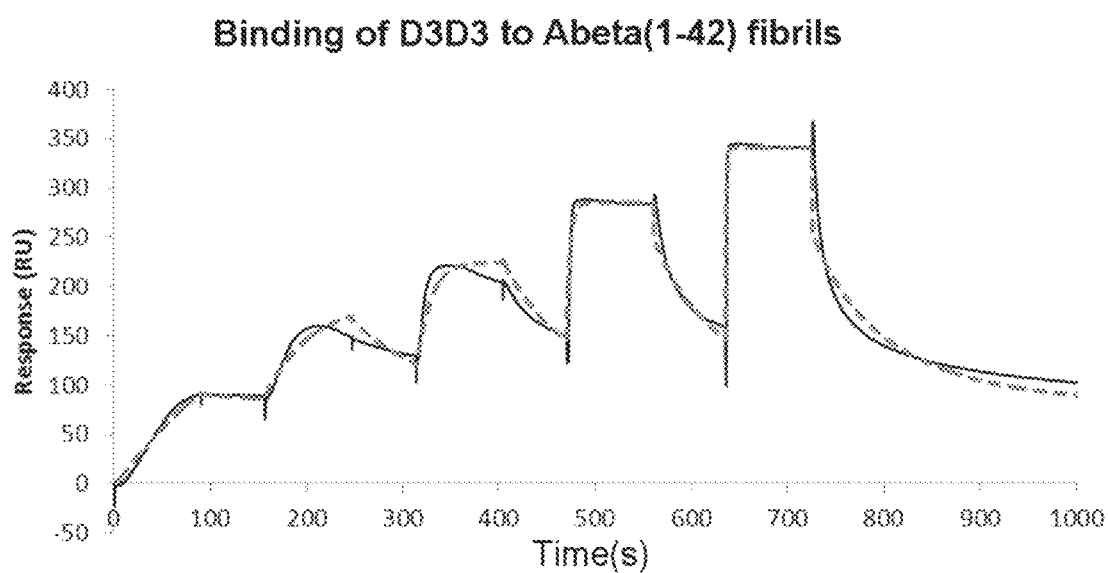

To obtain comparative quantitative affinity data for D3 and D3D3, Abeta-1-42 fibrils were prepared as described in Example 6. In contrast thereto, a mixture of 90% Abeta-1-42 and 10% of aminoterminally biotinylated Abeta-1-42 was used for the fibrilation experiment. To separate these fibrils from possible quantities of other Abeta conformers, for example monomers and amorphous oligomers, the fibril preparation was subjected to a density gradient centrifugation run as described in Example 4. Only the fibrils obtained in fractions 11 and 12 were subsequently employed as ligand in a surface plasmone resonance analysis. In doing so, they were immobilized on a streptavidin-coated chip (Sensor Chip SA). Thereafter, the affinities of the analytes D3 and D3D3 were determined by "single cycle kinetic" analysis. The analyte concentrations employed, the resulting sensorgrams (bold lines), the resulting fit curves (thin broken lines) and the result dissociation constants are comprised in FIGS. 5 and 6.

The results demonstrate that the D3 monomer binds to two slightly different binding sites with dissociation constants of 1.1 µM and 0.12 µM. The D3 dimer, too, binds to two different binding sites, one of which with a dissociation constant of 0.17 µM, which is similar to that of the D3 monomer, but the other with a dissociation constant of 8.8 pM, which is lower by several orders of magnitude. This demonstrates that polyvalent substances (here D3D3) bind almost 10000 times more strongly to their target than the corresponding monovalent substance (here D3).

What is claimed is:

1. A polymer which comprises at least two units which bind to amyloid-beta oligomers, wherein at least one of the at least two units is selected from SEQ ID NO:1, and homologs of this unit.

2. The polymer of claim 1, wherein at least one other of the at least two units is selected from SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, and homologs of the above-described units.

3. The polymer of claim 1, wherein the at least two units are identical or nonidentical.

4. The polymer of claim 1, wherein the polymer comprises 2, 3, 4, 5, 6, 7, 8, 9, 10 or more units which bind to amyloid-beta oligomers.

5. The polymer of claim 1, wherein the at least two units are peptides essentially composed of D-amino acids or antibodies or antibody fragments which bind to amyloid-beta.

6. The polymer of claim 1, wherein the at least two units are covalently or noncovalently linked to each other.

7. The polymer of claim 1, wherein the at least two units are linked to each other directly.

8. The polymer of claim 1, wherein the at least two units are linked to each other via a linker group.

9. The polymer of claim 1, wherein the at least two units are linked to each other in a linear or branched fashion.

10. The polymer of claim 1, wherein the polymer is a dendrimer and/or wherein the at least two units are linked to a platform molecule.

11. The polymer of claim 1, wherein each of the at least two units binds to a monomer and/or oligomer and/or fibrils of the amyloid-beta peptide with a dissociation constant ($K_D$ value) of not more than 500 μM.

12. The polymer of claim 1, wherein each of the at least two units binds to a monomer and/or oligomer and/or fibrils of the amyloid-beta peptide with a dissociation constant ($K_D$ value) of not more than 4 μM.

13. The polymer of claim 1, wherein the polymer binds amyloid-beta oligomers with a dissociation constant of not more than 1 μM.

14. The polymer of claim 13, wherein the polymer binds amyloid-beta oligomers with a dissociation constant of not more than 20 pM.

15. A pharmaceutical composition which comprises the polymer of claim 1.

16. A pharmaceutical composition which comprises the polymer of claim 13.

17. A kit, probe or composition which comprises the polymer of claim 1.

18. A process for preparing the polymer of claim 1, wherein the process comprises a peptide synthesis method or an organic synthesis method for low-molecular-weight compounds or wherein the polymer is prepared via a recombinant production of proteins.

* * * * *

```
                        SEQUENCE LISTING

<160> NUMBER OF SEQ ID NOS: 79

<210> SEQ ID NO 1
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 1

Pro Thr Leu His Thr His Asn Arg Arg Arg Arg Arg
1               5                   10

<210> SEQ ID NO 2
<211> LENGTH: 16
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 2

Lys Gln His His Val Glu Tyr Gly Ser Asp His Arg Phe Glu Ala Asp
1               5                   10                  15

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 3

Ser His Tyr Arg His Ile Ser Pro
1               5

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide
```

```
<400> SEQUENCE: 4

Gly Ile Ser Trp Gln Gln Ser His His Leu Val Ala
1               5                   10

<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 5

Pro Arg Thr Arg Leu His Thr His
1               5

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 6

Gln Ser His Tyr Arg His Ile Ser Pro Ala Gln Val
1               5                   10

<210> SEQ ID NO 7
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 7

Gln Ser His Tyr Arg His Ile Ser Pro Asp Gln Val
1               5                   10

<210> SEQ ID NO 8
<211> LENGTH: 11
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 8

Gln Ser His Tyr Arg His Ile Ser Pro Ala Arg
1               5                   10

<210> SEQ ID NO 9
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 9

Lys Ser His Tyr Arg His Ile Ser Pro Ala Lys Val
1               5                   10
```

```
<210> SEQ ID NO 10
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 10

Arg Pro Arg Thr Arg Leu His Thr His Arg Asn Arg
1               5                   10

<210> SEQ ID NO 11
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 11

Arg Pro Arg Thr Arg Leu His Thr His Arg Thr Glu
1               5                   10

<210> SEQ ID NO 12
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 12

Lys Pro Arg Thr Arg Leu His Thr His Arg Asn Arg
1               5                   10

<210> SEQ ID NO 13
<211> LENGTH: 24
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 13

Arg Pro Arg Thr Arg Leu His Thr His Arg Asn Arg Arg Pro Arg Thr
1               5                   10                  15

Arg Leu His Thr His Arg Asn Arg
            20

<210> SEQ ID NO 14
<211> LENGTH: 27
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 14

Arg Pro Arg Thr Arg Leu His Thr His Arg Asn Arg Asn Trp Asn Arg
1               5                   10                  15

Pro Arg Thr Arg Leu His Thr His Arg Asn Arg
            20                  25
```

```
<210> SEQ ID NO 15
<211> LENGTH: 24
<212> TYPE: PRT
<213> ORGANISM: Artificial Sequence
<220> FEATURE:
<223> OTHER INFORMATION: Description of Artificial Sequence: Synthetic
      D-Peptide
<220> FEATURE:
<223> OTHER INFORMATION: double-D3-free-Ntermini (rprtrlhthrnr)2-PEG3

<400> SEQUENCE: 15

Arg Pro Arg Thr Arg Leu His Thr His Arg Asn Arg Arg Pro Arg Thr
1               5                   10                  15

Arg Leu His Thr His Arg Asn Arg
            20

<210> SEQ ID NO 16
<211> LENGTH: 24
<212> TYPE: PRT
<213> ORGANISM: Artificial Sequence
<220> FEATURE:
<223> OTHER INFORMATION: Description of Artificial Sequence: Synthetic
      D-Peptide
<220> FEATURE:
<223> OTHER INFORMATION: double-D3-free-Ctermini: PEG5-(rprtrlhthrnr)2

<400> SEQUENCE: 16

Arg Pro Arg Thr Arg Leu His Thr His Arg Asn Arg Arg Pro Arg Thr
1               5                   10                  15

Arg Leu His Thr His Arg Asn Arg
            20

<210> SEQ ID NO 17
<211> LENGTH: 11
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 17

Asp Ala Glu Phe Arg His Asp Ser Gly Tyr Glu
1               5                   10

<210> SEQ ID NO 18
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 18

His His Gly His Ser Pro Asn Val Ser Gln Val Arg
1               5                   10

<210> SEQ ID NO 19
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 19

Gly Ser Phe Ser Thr Gln Val Gly Ser Leu His Arg
1               5                   10
```

<210> SEQ ID NO 20
<211> LENGTH: 11
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 20

His Thr Gly Thr Gln Ser Tyr Val Pro Arg Leu
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 21

Thr Leu Ala Tyr Ala Arg Ala Tyr Met Val Ala Pro
1               5                   10

<210> SEQ ID NO 22
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 22

Thr Leu Ala Tyr Ala Arg Ala Tyr Met Val Ala Pro
1               5                   10

<210> SEQ ID NO 23
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 23

Ala Thr Pro Gln Asn Asp Leu Lys Thr Phe Pro His
1               5                   10

<210> SEQ ID NO 24
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 24

Thr Gln Pro Glu Thr Asp Leu Leu Arg Val Gln Phe
1               5                   10

<210> SEQ ID NO 25
<211> LENGTH: 11
<212> TYPE: PRT
<213> ORGANISM: Artificial Sequence
<220> FEATURE:
<223> OTHER INFORMATION: Description of Artificial Sequence: Synthetic
      D-Peptide

```
<400> SEQUENCE: 25

Cys Ile Thr Trp Pro Pro Thr Gly Leu Thr Tyr
1               5                   10

<210> SEQ ID NO 26
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 26

Thr Phe Leu Glu Thr Gly Pro Ile Tyr Ala Asp Gly
1               5                   10

<210> SEQ ID NO 27
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 27

Leu Val Pro Pro Thr His Arg His Trp Pro Val Thr
1               5                   10

<210> SEQ ID NO 28
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 28

Ala Pro Pro Gly Asn Trp Arg Asn Tyr Leu Met Pro
1               5                   10

<210> SEQ ID NO 29
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 29

Asp Asn Tyr Ser Asn Tyr Val Pro Gly Thr Lys Pro
1               5                   10

<210> SEQ ID NO 30
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 30

Ser Val Ser Val Gly Met Lys Pro Ser Pro Arg Pro
1               5                   10
```

```
<210> SEQ ID NO 31
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 31

Ser Leu Pro Asn Pro Phe Ser Val Ser Ser Phe Gly
1               5                   10

<210> SEQ ID NO 32
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 32

Tyr Val His Asn Pro Tyr His Leu Pro Asn Pro Pro
1               5                   10

<210> SEQ ID NO 33
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 33

Cys Arg Arg Leu His Thr Tyr Ile Gly Pro Val Thr
1               5                   10

<210> SEQ ID NO 34
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 34

Gly Ala Thr Met Lys Met Asp Asp His Thr Val
1               5                   10

<210> SEQ ID NO 35
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 35

Leu Gly Lys Thr Gln Lys Leu Ser Asp Ala His Ser
1               5                   10

<210> SEQ ID NO 36
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide
```

```
<400> SEQUENCE: 36

Asp Asp Gln Ala Arg Pro Tyr Met Ala Tyr Gly Pro
1               5                   10

<210> SEQ ID NO 37
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 37

Gly Asp Thr Trp Val Asn Met Val Ser Met Val His
1               5                   10

<210> SEQ ID NO 38
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 38

Gly Tyr Thr Trp Val Asn Met Val Ser Met Val His
1               5                   10

<210> SEQ ID NO 39
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 39

Trp Thr Asn Thr Val Ala Arg Leu Ala Thr Pro Tyr
1               5                   10

<210> SEQ ID NO 40
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 40

Gln Thr Gln Ala Leu Tyr His Ser Arg Gln Val His
1               5                   10

<210> SEQ ID NO 41
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 41

Asn Ser Gln Thr Gln Thr Leu His Leu Phe Pro His
1               5                   10
```

```
<210> SEQ ID NO 42
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 42

His Asn Thr Ser Ala Asn Ile Leu His Ser Ser His
1               5                   10

<210> SEQ ID NO 43
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 43

Ser His Ile Asn Pro Thr Ser Phe Trp Pro Ala Pro
1               5                   10

<210> SEQ ID NO 44
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 44

Thr Phe Ser Asn Pro Leu Tyr Met Trp Pro Arg Pro
1               5                   10

<210> SEQ ID NO 45
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 45

Gly Pro Ser Pro Phe Asn Pro Gln Pro Thr Pro Val
1               5                   10

<210> SEQ ID NO 46
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 46

Phe Ser Asp His Lys Ser Pro Thr Pro Pro Pro Arg
1               5                   10

<210> SEQ ID NO 47
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide
```

```
<400> SEQUENCE: 47

Ser Thr Ser Val Tyr Pro Pro Pro Ser Ala Trp
1               5                   10

<210> SEQ ID NO 48
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 48

Tyr Gly Leu Pro Thr Gln Ala Asn Ser Met Gln Leu
1               5                   10

<210> SEQ ID NO 49
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 49

His Asn Arg Thr Asp Asn Thr Tyr Ile Arg Pro Thr
1               5                   10

<210> SEQ ID NO 50
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 50

Leu Gln Gln Pro Leu Gly Asn Asn Arg Pro Asn Ser
1               5                   10

<210> SEQ ID NO 51
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 51

Lys Pro Glu Asp Ser Ala Ala Tyr Pro Gln Asn Arg
1               5                   10

<210> SEQ ID NO 52
<211> LENGTH: 13
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 52

Arg Pro Glu Asp Ser Val Ile Thr Lys Thr Gln Asn Thr
1               5                   10
```

```
<210> SEQ ID NO 53
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 53

Arg Ala Ala Asp Ser Gly Cys Thr Pro Thr Lys His
1               5                   10

<210> SEQ ID NO 54
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 54

Arg Pro Arg Thr Arg Leu His Thr His Arg Asn Thr
1               5                   10

<210> SEQ ID NO 55
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 55

Arg Pro Arg Thr Arg Leu His Thr His Thr Asn Val
1               5                   10

<210> SEQ ID NO 56
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 56

Arg Pro Arg Thr Arg Leu His Thr His Thr Asn Arg
1               5                   10

<210> SEQ ID NO 57
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 57

Arg Pro Arg Thr Arg Leu His Thr His Arg Lys Gln
1               5                   10

<210> SEQ ID NO 58
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide
```

```
<400> SEQUENCE: 58

Arg Pro Arg Thr Arg Leu His Thr Leu Arg Asn Arg
1               5                   10

<210> SEQ ID NO 59
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 59

Arg Arg Arg Ser Pro Leu His Thr His Arg Asn Arg
1               5                   10

<210> SEQ ID NO 60
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 60

Leu Arg Ser Pro Arg Gln Arg Arg Ile Pro Arg Ile
1               5                   10

<210> SEQ ID NO 61
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 61

Arg Lys Arg Gln Leu Arg Met Thr Thr Pro Arg Pro
1               5                   10

<210> SEQ ID NO 62
<211> LENGTH: 11
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 62

Ser His Tyr Arg His Ile Ser Pro Ala Gln Lys
1               5                   10

<210> SEQ ID NO 63
<211> LENGTH: 24
<212> TYPE: PRT
<213> ORGANISM: Artificial Sequence
<220> FEATURE:
<223> OTHER INFORMATION: Description of Artificial Sequence: Synthetic
      D-Peptide
<220> FEATURE:
<223> OTHER INFORMATION: double-D3-free-Ntermini (rprtrlhthrnr)2

<400> SEQUENCE: 63

Arg Pro Arg Thr Arg Leu His Thr His Arg Asn Arg Arg Pro Arg Thr
1               5                   10                  15

Arg Leu His Thr His Arg Asn Arg
            20
```

```
<210> SEQ ID NO 64
<211> LENGTH: 24
<212> TYPE: PRT
<213> ORGANISM: Artificial Sequence
<220> FEATURE:
<223> OTHER INFORMATION: Description of Artificial Sequence: Synthetic
      D-Peptide
<220> FEATURE:
<223> OTHER INFORMATION: double-D3-free-Ctermini: (rprtrlhthrnr)2

<400> SEQUENCE: 64

Arg Pro Arg Thr Arg Leu His Thr His Arg Asn Arg Pro Arg Thr
1               5                   10                  15

Arg Leu His Thr His Arg Asn Arg
            20

<210> SEQ ID NO 65
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 65

Arg Pro Ile Thr Arg Leu Arg Thr His Gln Asn Arg
1               5                   10

<210> SEQ ID NO 66
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 66

Arg Pro Arg Thr Arg Leu His Thr His Arg Asn Arg
1               5                   10

<210> SEQ ID NO 67
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 67

Pro Asn His His Arg Arg Arg Arg Thr Thr Leu
1               5                   10

<210> SEQ ID NO 68
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 68

Arg Arg Pro Thr Leu Arg His Thr His Asn Arg Arg
1               5                   10

<210> SEQ ID NO 69
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      D-Peptide

<400> SEQUENCE: 69

Arg Pro Arg Thr Arg Leu Arg Asn Arg
1               5

<210> SEQ ID NO 70
<211> LENGTH: 6
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 70

Arg Pro Arg Thr Arg Leu
1               5

<210> SEQ ID NO 71
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 71

Arg Pro Ile Thr Arg Leu His Thr Asp Arg Asn Arg
1               5                   10

<210> SEQ ID NO 72
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 72

Arg Pro Ile Thr Thr Leu Gln Thr His Gln Asn Arg
1               5                   10

<210> SEQ ID NO 73
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 73

Arg Pro Arg Thr Arg Leu Arg Thr His Gln Asn Arg
1               5                   10

<210> SEQ ID NO 74
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 74

Arg Pro Ile Thr Arg Leu Gln Thr His Glu Gln Arg
1               5                   10
```

```
<210> SEQ ID NO 75
<211> LENGTH: 18
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 75

Arg Pro Arg Thr Arg Leu Arg Asn Arg Arg Pro Arg Thr Arg Leu Arg
1               5                   10                  15

Asn Arg

<210> SEQ ID NO 76
<211> LENGTH: 24
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 76

Pro Thr Leu His Thr His Asn Arg Arg Arg Arg Pro Thr Leu His
1               5                   10                  15

Thr His Asn Arg Arg Arg Arg Arg
            20

<210> SEQ ID NO 77
<211> LENGTH: 12
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 77

Ser Gly Trp His Tyr Asn Trp Gln Tyr Trp Trp Lys
1               5                   10

<210> SEQ ID NO 78
<211> LENGTH: 20
<212> TYPE: PRT
<213> ORGANISM: Artificial Sequence
<220> FEATURE:
<223> OTHER INFORMATION: Description of Artificial Sequence: Synthetic
      D-Peptide

<400> SEQUENCE: 78

Arg Pro Arg Thr Arg Ser Gly Trp His Tyr Asn Trp Gln Tyr Trp Trp
1               5                   10                  15

Lys Arg Asn Arg
            20

<210> SEQ ID NO 79
<211> LENGTH: 20
<212> TYPE: PRT
<213> ORGANISM: Artificial Sequence
<220> FEATURE:
<223> OTHER INFORMATION: Description of Artificial Sequence: Synthetic
      D-Peptide
```

<400> SEQUENCE: 79

```
Pro Thr Leu Ser Gly Trp His Tyr Asn Trp Gln Tyr Trp Trp Lys Arg
1               5                   10                  15

Arg Arg Arg Arg
            20
```